United States Patent [19]

Okamoto et al.

[11] Patent Number: 4,628,531
[45] Date of Patent: Dec. 9, 1986

[54] PATTERN CHECKING APPARATUS

[75] Inventors: Keiichi Okamoto, Yokohama; Kozo Nakahata, Chigasaki; Yukio Matsuyama; Hideaki Doi, both of Yokohama; Susumu Aiuchi; Mineo Nomoto, both of Yokohama, all of Japan

[73] Assignee: Hitachi, Ltd., Tokyo, Japan

[21] Appl. No.: 583,867

[22] Filed: Feb. 27, 1984

[30] Foreign Application Priority Data

Feb. 28, 1983 [JP] Japan .................................. 58-30829

[51] Int. Cl.$^4$ ............................................. G06K 9/00
[52] U.S. Cl. ...................................... 382/8; 356/237; 356/394; 382/34
[58] Field of Search ........................ 382/8, 30, 34, 27; 356/237, 394; 358/106

[56] References Cited

U.S. PATENT DOCUMENTS

| 3,887,762 | 6/1975 | Uno et al. ............................ 358/106 |
| 3,905,045 | 9/1975 | Nickel .................................... 382/6 |
| 4,200,861 | 4/1980 | Hubach et al. ....................... 382/30 |
| 4,309,691 | 1/1982 | Castleman ............................ 382/6 |
| 4,345,312 | 8/1982 | Yasuye et al. ....................... 382/34 |
| 4,352,125 | 9/1982 | Guth ................................... 358/106 |

FOREIGN PATENT DOCUMENTS 59-13890  4/1984  Japan ................................. 356/237

OTHER PUBLICATIONS

Ejiri et al., "A Process for Detecting Defects in Complicated Patterns", 1973.
Adam Osborne, An Introduction to Microcomputers, 1980.

Primary Examiner—Leo H. Boudreau
Attorney, Agent, or Firm—Antonelli, Terry & Wands

[57] ABSTRACT

A pattern checking apparatus carries out the detection of candidate defects through a primary selection with a sensitivity high enough to detect any existing defect, and then carries out a detailed analysis by a controlling processor for a pattern including the periphery of the detected candidate defect through a secondary selection in which a candidate defect which is not a defect in a practical sense is removed from candidates, so that only real defects are detected.

9 Claims, 20 Drawing Figures

STANDARD (MODEL) PATTERN

FIG. 10b

DETECTED (SAMPLE) PATTERN

PATTERN CHECKING APPARATUS

The present invention relates to a pattern checking apparatus and, particularly, to a high-speed pattern inspection system for checking patterns on printed boards or integrated circuit wafers, patterns on masks used to fabricate printed boards or integrated circuits, or the like.

Figure 1:
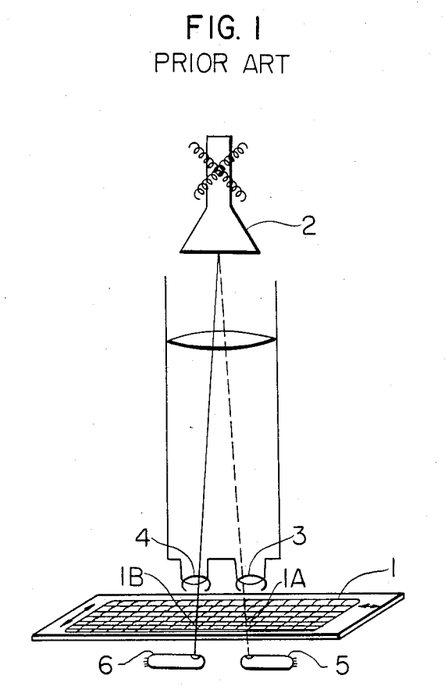
FIG. 1 is an illustration showing, as an example, the pattern detecting part of a conventional pattern checking apparatus.

FIG. 1 shows the pattern detecting part of a conventional pattern checking apparatus as disclosed, for example, in Japanese Patent Publication No. 54-37475. This apparatus performs defect detection for patterns on a mask 1 for fabrication of integrated circuits by comparing two chip patterns 1A and 1B on the mask 1 based on the fact that the mask includes a number of repeated chip patterns of the same circuit configuration and that the probability of defects of the same appearance existing at the same position of each chip is negligibly small. The apparatus operates in such a way that a flying spot scanner 2 projects light spots through objective lenses 3 and 4 onto corresponding positions of the chip patterns 1A and 1B on the mask 1, and photo-electric detectors 5 and 6 transform the pattern images into electrical signals so that the signals are compared with each other.

Figure 2:
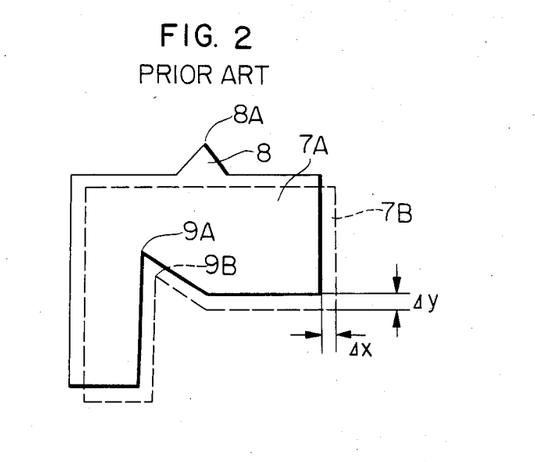
FIG. 2 is a diagram used to explain the defect detection principle of the apparatus shown in FIG. 1.

FIG. 2 shows the principle of defect detection in the above-mentioned apparatus. Due to errors in optical and mechanical systems, it is not possible to make a completely registrated relation between corresponding pattern portions 7A and 7B (shown by the solid line and dashed line) of the chip patterns 1A and 1B. Therefore, the patterns are compared under registering or errors of, for example, $\Delta x$ and $\Delta y$. The existence of anti-coincident portions of the chip patterns 1A and 1B may be detected as a defect, and portions which are normal but anti-coincident with each other due to the above-mentioned registering errors could erroneously be detected as defects.

To eliminate the detection of such pseudo defects, this conventional technique allows the maximum tolerable values $\delta_x$ and $\delta_y$ for registering errors $\Delta x$ and $\Delta y$ which cannot be avoided between normal patterns and it is devised to detect only anti-coincidence ouside the tolerable range such as, for example, a portion 8 of the chip pattern 7A.

One problem of this apparatus is that a defect smaller than the registering error cannot be detected in principle. Recently-used masks for fabricating LSIs have the minimum dimension as small as 1-2 $\mu$m, and a defect of 1 $\mu$m or less needs to be detected. This necessitates the positioning accuracy of scanning to be maintained within 1 $\mu$m, that is a very difficult requirement for the available mechanical and optical systems.

Another prior art apparatus as disclosed, for example, in Japanese Patent Application Laid-Open No. 50-131469, proposes to overcome the above-mentioned deficiency by first making the image of features of patterns to be compared and then comprising the pattern features with each other. The principle of this apparatus will be described in connection with FIG. 2. If attention is paid, for example, to small pattern elements as features of a pattern, small pattern elements 8A and 9A will be detected on the partial pattern 7A of the chip pattern 1A. On the other hand, only a small pattern element 9B will be detected on the partial pattern 7B of a chip pattern 1B. Then, these pattern features are compared. For the element 9A detected on the partial pattern 7A, the element 9B detected on the partial pattern 7B exists within the range of registering error. For the element 8A detected on the partial pattern 7A, on the other hand, no corresponding element exists on the partial pattern 7B. Thus, this apparatus enables the detection of defects smaller than the registering error by comparing pattern features within a distance range larger than the registering error.

The latter apparatus is more effective in detecting defects smaller than the registering error as compared with the previous apparatus in which patterns are compared directly. However, the ability of defect detection depends on the type of pattern features to be selected. Namely, since there are infinite types of defects, feature extracters for recognizing every defect type will be needed when all types of defects are to be detected. A large-scale hardware will be required to realize such a function, resulting naturally in an increased construction cost, or, if the function is accomplished by way of software, an enormous checking time will be required.

It is an object of the present invention to provide an inexpensive pattern checking apparatus which has a greatly increased sensitivity of defect detection and is capable of preventing erroneous detection so as to perform reliable and fast pattern checking.

According to the present invention, a pattern to be checked is compared with a standard pattern so as to extract candidate defects by picking up anti-coincident portions or defect-like portions, and the candidates are checked in further detail with reference to the checking criterion.

At the first step, the "primary selection" is carried out through the detection which is sensitive enough to detect any small defect. Next, a pattern portion including detected candidate defects is subjected to detailed analysis by a controlling processor (e.g., computer) so as to carry out the "secondary selection" by which a comparison result which is not a defect in a practical sense is removed from candidate defects. In this case, most of the pseudo defects are considered to be caused by the above-mentioned positioning error, and if they were included in candidate defects of the "primary selection", a great number of candidate defects would need to be processed beyond the capacity of the processor. Therefore, positioning is corrected thoroughly so as to prevent such pseudo defects from being included in candidate defects.

While the detailed analysis is carried out by the processor, pattern data is stored in a buffer memory so that it is not lost during the analysis and, as a result, errors in checking are not likely to occur. In this way, defect detection on a real-time basis is achieved.

The present invention will be more apparent from the following detailed description taken in conjunction with the accompanying drawings, in which.

Figure 3:
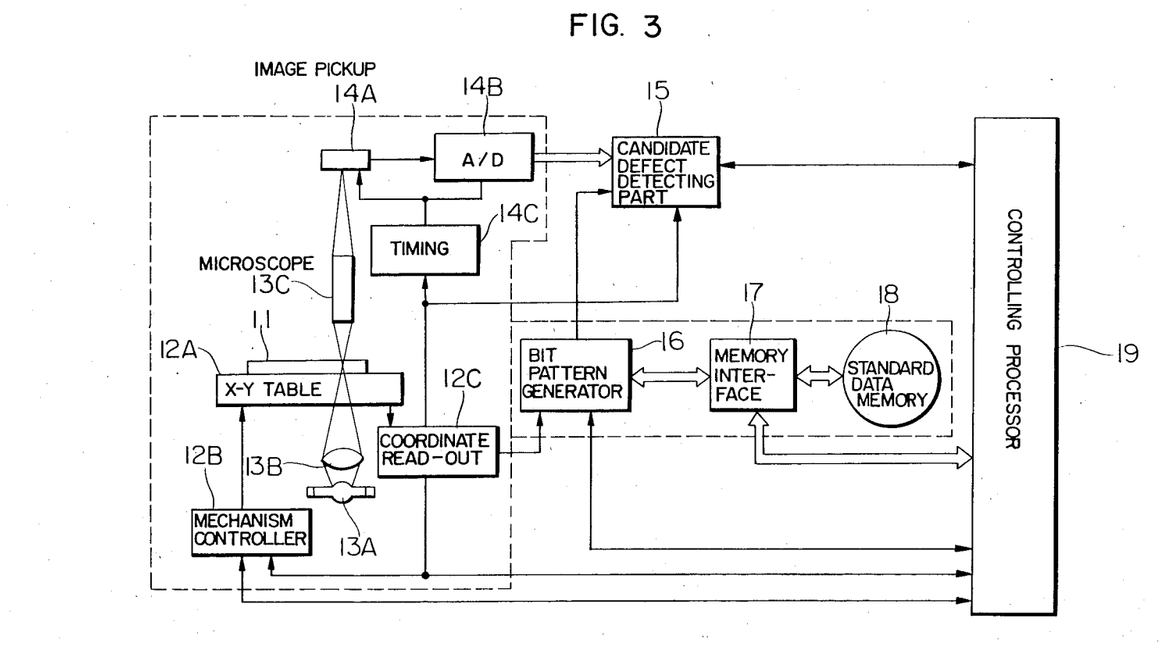
FIG. 3 is a block diagram of a pattern checking apparatus embodying the present invention.
Figure 4A:
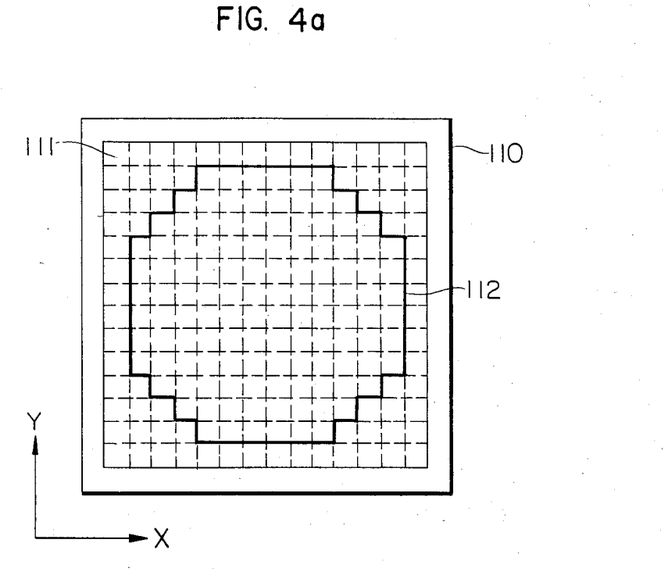
FIGS. 4a and 4b are diagrams used to explain two-dimensional pattern scanning carried out by the apparatus.
Figure 4B:
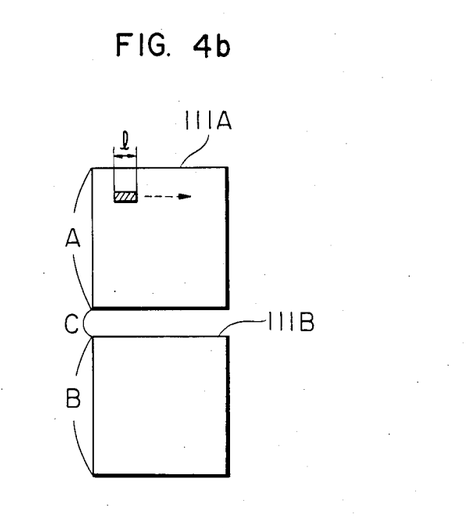
Figure 5:
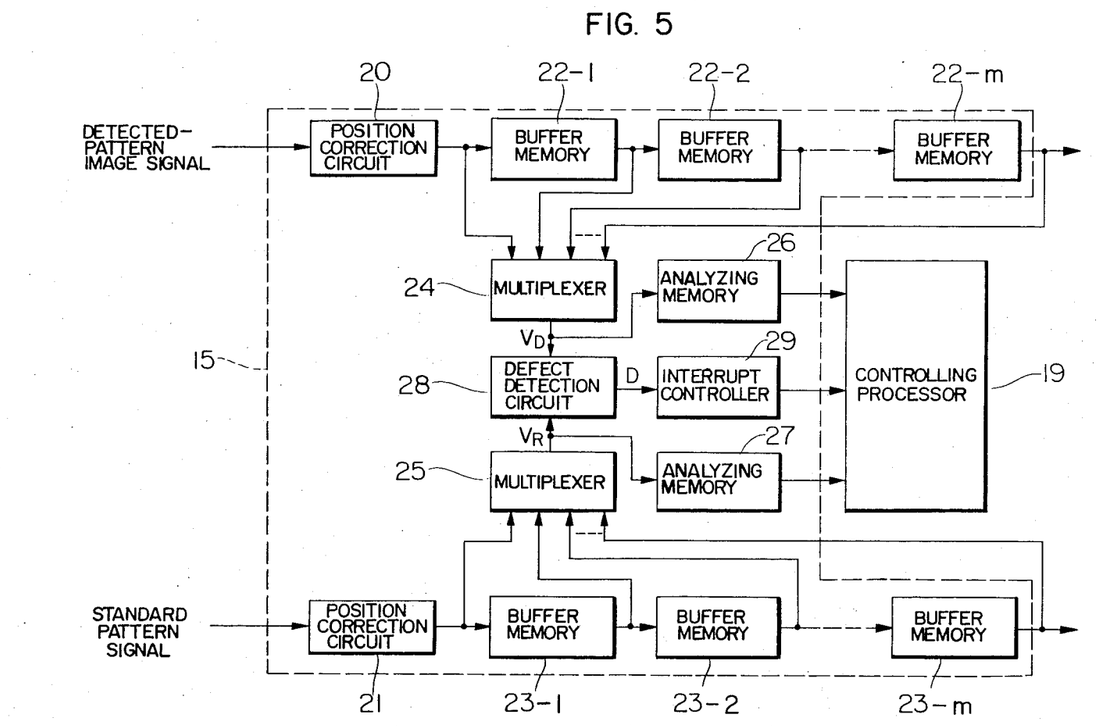
FIG. 5 is a block diagram showing an example of a candidate defect detecting part in the apparatus.
Figure 6:
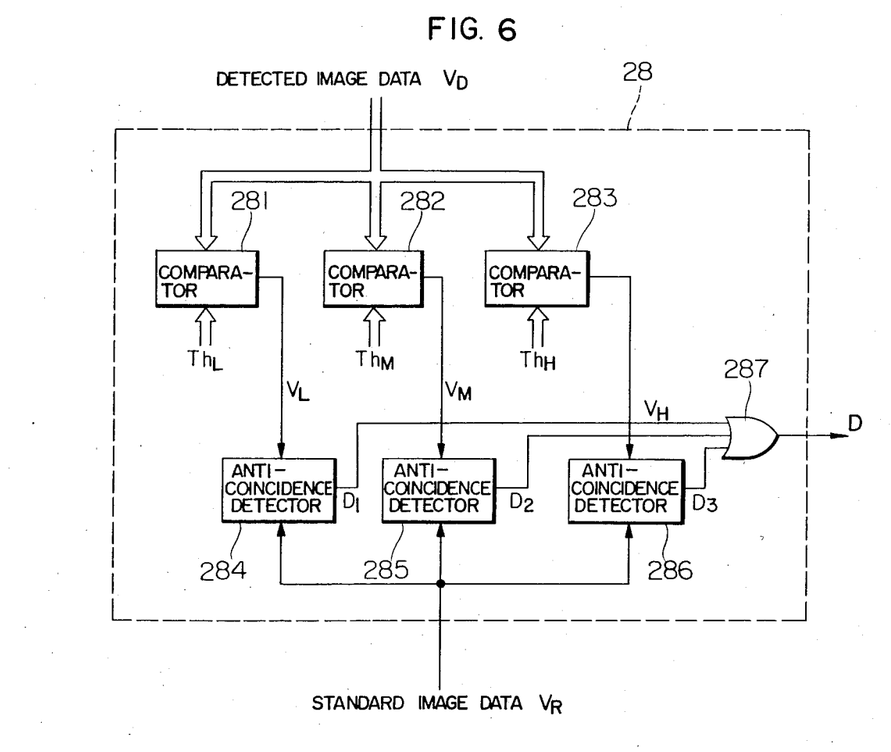
FIG. 6 is a block diagram showing an example of a defect detection circuit in the apparatus.
Figure 7:
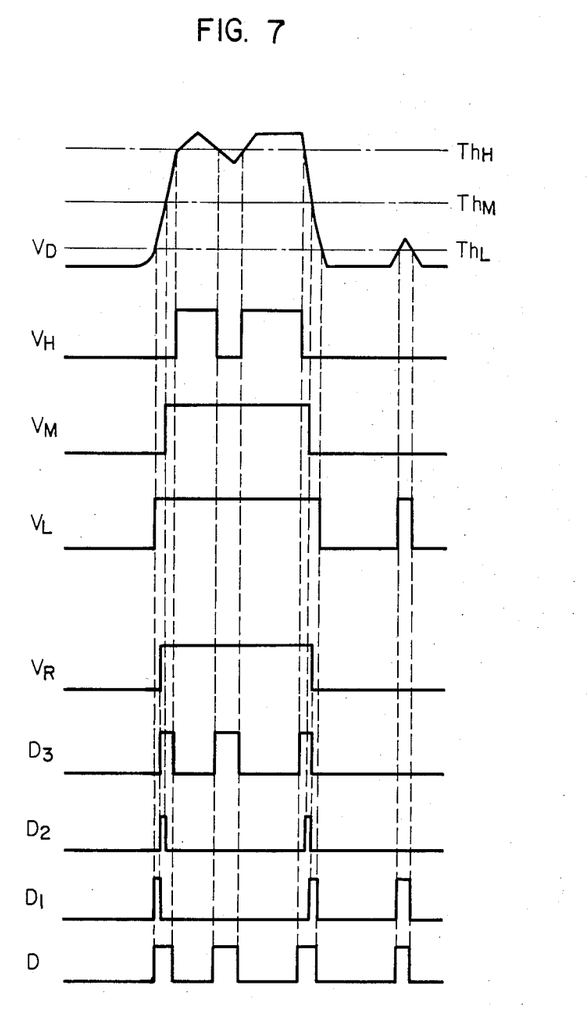
FIG. 7 is a set of timing charts used to explain the operation of the defect detection circuit.

Preferred embodiments of the present invention will now be described with reference to the drawings. FIG. 3 is a block diagram showing a pattern checking apparatus embodying the present invention. The apparatus is used, for example, for pattern checking or defect detection of photo-masks for fabricating semiconductor integrated circuits. FIGS. 4a and 4b are diagrams used to explain two-dimensional pattern scanning employed by the apparatus, FIG. 5 is a block diagram showing an example of a candidate defect detecting part in the apparatus, FIG. 6 is a block diagram showing an example of a defect detection circuit in the apparatus, and FIG. 7 is a set of timing charts used to explain the operation of the defect detection circuit.

Reference numeral 11 represents a mask to be checked, and numerals 12, 13 and 14 represents a scanning and imaging part including an X-Y table 12A, a mechanism controller 12B, a coordinate read-out unit 12C, an illuminating light source 13A, a condenser lens 13B, a microscope 13C, an image pickup unit 14A, an A/D converter 14B, and a timing circuit 14C. Numeral 15 represents a candidate defect detecting part. Numerals 16, 17 and 18 represent a standard pattern data generating part, made up of a bit pattern generator 16, a memory interface circuit 17, and a standard data memory 18. Numeral 19 represents a controlling processor.

The mask 11 placed on the X-Y table 12A is illuminated transparently by means of the light source 13A and the condenser lens 13B. A pattern image of the mask 11 is magnified by the microscope 13C and the optical pattern image is transformed into an electrical video signal by the image pickup unit 14A. The signal is converted by the A/D converter 14B into a detected pattern image signal in a digital form. Standard data stored in the standard data memory 18, such as a magnetic tape unit, is supplied through the memory interface circuit 17 to the bit pattern generator 16 which in turn generates a standard pattern. The detected pattern image signal from the A/D converter 14B is compared with the standard pattern data by the candidate defect detecting part 15 on a real-time basis to detect candidate defects. The bit pattern generation is well known and explanation thereof will be omitted.

Next, in order to facilitate a general understanding of the apparatus, two-dimensional scanning for the whole mask 11 will be described. The mask 11 under test is generally made of a glass plate 110 on which a number of repeated functional patterns 111 of a chip (one integrated circuit also is called a die) are regularly arranged in the X and Y directions as shown in FIG. 4a. The X-Y table 12A having the mask 11 mounted thereon is driven by the mechanism controller 12B in accordance with preset data so that the whole mask 11 is scanned.

The scanning operation is shown in FIG. 4b. Chip patterns including patterns 111A and 111B are scanned in such a manner that while using the image pickup unit 14A having a detection width (sensor width) of 1, the X-Y table 12A is moved to scan the mask in the X direction until the end of an effective area 112 of the mask is reached at which time the table is moved in the Y direction by one scanning line, and then the table is moved in the X direction but oppositely with respect to the previous scanning. These operations are repeated until a two-dimensional pattern scanning for the entire mask is completed. In FIG. 4b, portions indicated by A and B are effective chip sections while a portion indicated by C is a dicing area.

Next, a concrete arrangement of the candidate defect detecting part 15 will be described in more detail. The following conditions are established in the pattern checking apparatus.

(I) The accuracy of the X-Y table 12A for mounting the mask 11 to be checked and the accuracy of the mask printing are within a few $\mu$m in the whole area of the mask. Namely, a pattern detection error which can occur when the image pickup unit scans one chip is within 0.1–0.2 $\mu$m.

(II) When a real defect is detected, a certain area around the defect is not necessary to be checked.

(III) The boundary areas between chips, i.e., dicing areas, need not be checked.

The operation of the candidate defect detecting part 15 will be described with reference to FIG. 5. The detected pattern image signal having a digital value derived through the A/D converter 14B from the analog image signal of the mask pattern detected by the image pickup unit 14 is supplied to a multiplexer 24 through a position correction circuit 20 which modifies the two-dimensional output position in response to the command from the controlling processor 19. The signal is also supplied sequentially to buffer memories 22-1 through 22-m. In FIG. 5, a command signal line from the controlling processor 19 to the position correction circuit 20 is not shown for purposes of simplicity. The buffer memories 22 are made up of shift registers for storing temporarily image data in a certain time frame, and a positional displacement correcting function is provided at the image data output section. This type of buffer memory is available, for example, as 2-port or dual-port memory. In this case, data is written in one address and read out from another address so as to achieve a certain displacement of output data and, consequently, the positional displacement can be corrected.

Outputs of the buffer memories 22 with the displacement correcting function are supplied to an input of the multiplexer 24, so that one of an output of the position correction circuit 20 and outputs of the buffer memories 22 is selected to form an input $V_D$ to the defect detection circuit 28 and also to an analyzing memory 26 which stores candidate defect image data to be analyzed later by the controlling processor 19.

The standard pattern data from the bit pattern generator 16 is supplied through a position correction circuit 21 to a multiplexer 25, and also supplied sequentially to buffer memories 23-1 through 23-m. The buffer memories 23 are used for the same purpose as the buffer memories 22, and the output from each output section thereof having a positional displacement correcting function as in the case of the buffer memories 22 is supplied to the multiplexer 23 and also to the following buffer memory 23. An output $V_R$ of the multiplexer 25 is supplied to the defect detection circuit 28 and the analyzing memory 27 whose contents are read out later by the controlling processor 19 for analysis.

Initially, the position correction circuit 20 and the displacement corrector portions of the buffer memories 22 and 23 are set to the center of the correctable range in response to the command from the controlling processor 19. (The command signal line is not shown in the figure.) In the initial state, the multiplexers 24 and 25 select the outputs of the position correcting circuits 20 and 21, respectively, so that the defect detection circuit 28 receives the detected-pattern video signal and the standard pattern signal. The defect detection circuit 28 is capable of determining a defect on a real-time basis (at the rate of image data sampling by the image pickup unit 14A).

The defect detecting function will be described with reference to FIG. 6. The multiplexer 24 for the detected image data provides image data $V_D$ representing multi-value information and it is expressed digitally due to the A/D converter 14B. On the other hand, comparators 281, 282 and 283 are designed to receive two-value image data $V_L$, $V_M$ and $V_H$ in accordance with respective low, medium and high threshold values $Th_L$, $Th_M$ and $Th_H$ given by the controlling processor 19. (The threshold input lines are not shown in FIG. 5.)

The relationship between the three threshold values and the detected image data is shown in FIG. 7, where the digital data is depicted as an analog waveform for purposes of easy understanding. As shown in the figure, the detected image signal for a small pattern, even if it is produced intrinsically from black-white two-value patterns as of a photo-mask, does not provide a 100% contrast due to the deficient resolution of the optical system. Therefore, a plurality of threshold values are provided so that small patterns can be detected.

The two-value image data $V_L$, $V_M$ and $V_H$ are compared with the standard image data $V_R$ by respective anti-coincidence detectors 284, 285 and 286. In this case, anti-coincidence outputs as shown by $D_1$, $D_2$ and $D_3$ are produced. The anti-coincidence outputs include the case of incorrect positioning between the standard image data $V_R$ and the detected image data $V_D$ and the case of a real defect. The logical sum of the three anti-coincidence outputs are taken by an OR gate 287, which produces the candidate defect detection output signal D of the defect detection circuit 28. The comparators 281-283 are, of course, designed such that an error which cannot be avoided even through the positional correction, e.g., one bit of quantization error, is counted out of the positioning error when the inconsistent part of the detected image data $V_D$ from the standard data $V_R$ is within the unavoidable error. Namely, only real defect signals excluding those which include the unavoidable positioning error constitute the candidate defect detection signal D. The dead band of the comparators 281, 282 and 283 for preventing the detection of pseudo defects caused by the positioning error can be made far smaller than that of the foregoing prior art apparatus owing to the function of the positioning circuit as will be described later.

Figure 8A:
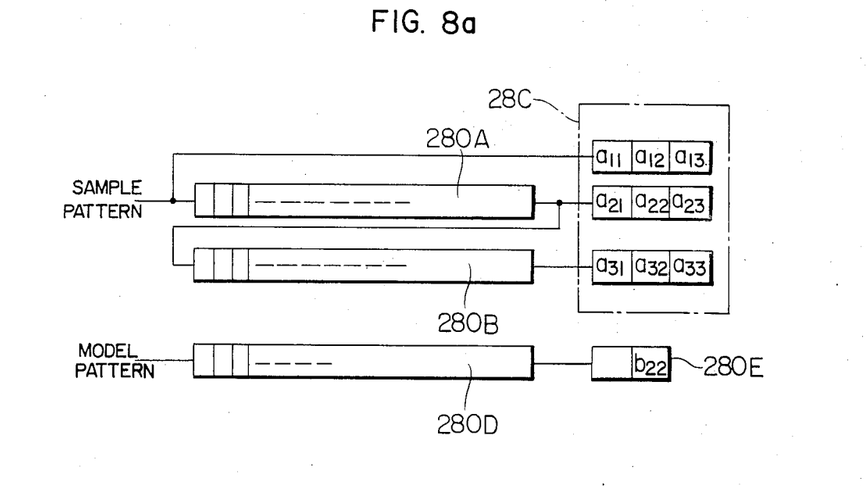
FIGS. 8a and 8b are block diagrams showing an example of an image segmentation circuit.

The defect detecting operation will further be described in detail. First, windowing of image will be described with reference to FIGS. 8a and 8b which are block diagrams showing an example of the image windowing circuit provided in the defect detection circuit 28. As shown in FIG. 8a, a partial image consisting of 3-by-3 picture elements is taken from the sample under test. The circuit arrangement includes serial-in/serial-out shift registers 280A and 280B for storing image data for one scanning line provided by the image pickup unit 14A, and a serial-in/parallel-out shift register 280C for reading out the image data in a parallel fashion. The circuit arrangement for the model includes a serial-in/serial-out shift register 280D and a serial-in/parallel-out shift register 280E, and operates to provide a partial image corresponding to the central picture element in the 3-by-3 partial image of the sample.

Figure 8B:
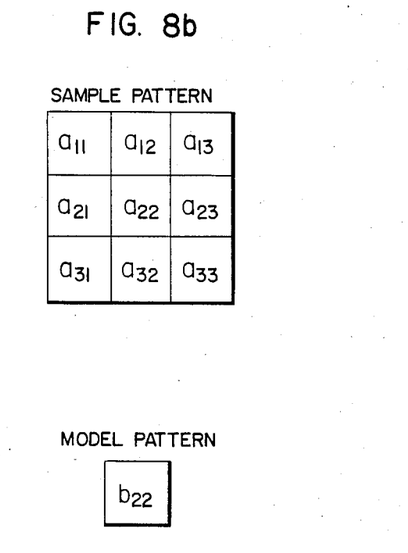

The method of determining a defect with the ±1 bit tolerance for positioning will be described with reference to FIG. 8b. The model picture element $b_{22}$ corresponds in phase (position) to $a_{22}$ of the 3-by-3 sample picture elements. For $b_{22}=$"1", when all of $a_{21}$, $a_{22}$ and $a_{23}$ are "0", it is determined to be defective as the detection of anti-coincidence in the horizontal direction. For $b_{22}=$"0", when all of $a_{21}$, $a_{22}$ and $a_{23}$ are "1", it is determined to be defective as the detection of anti-coincidence in the horizontal direction.

Figure 9:
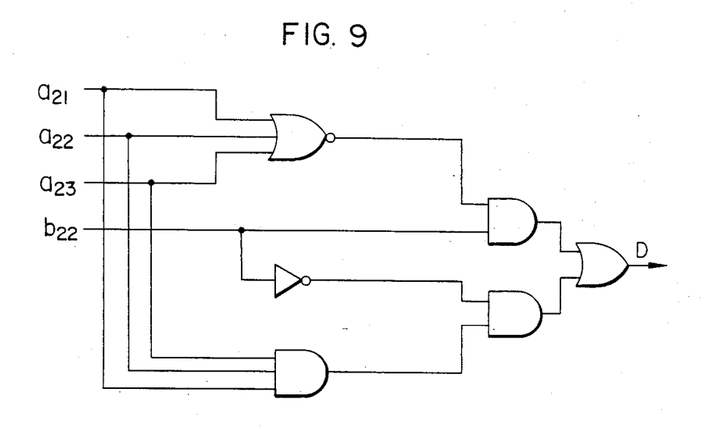
FIG. 9 is a block diagram showing an example of an anti-coincidence detector in the apparatus.

FIG. 9 is a block diagram showing one embodiment of the anti-coincidence detector provided as a logic circuit. The circuit has input signals $a_{21}$, $a_{22}$, $a_{23}$ and $b_{22}$ corresponding to the picture elements shown in FIG. 8b, and it will readily be understood that this logic circuit arrangement provides the anti-coincidence output. This is an example of a circuit for the detection of anti-coincidence with the ±1 bit tolerance of positioning error in the horizontal direction. Through the application of the circuit to the vertical and oblique directions, the difference of 2 bits or more between the sample and model is detected as a defect while allowing the positional displacement of ±1 bit in each direction.

The candidate defect signal D issues an interrupt request through an interrupt controller 29 to the controlling processor 19, which then halts the entry of image data to the analyzing memories 26 and 27. (The halt command signal line is not shown in FIG. 5.) Subsequently, image data including a candidate defect image stored in the analyzing memory 26 is compared with standard image data stored in the analyzing memory 27, and detailed analysis ("secondary selection") is carried out.

The positioning error and pseudo defect caused by the improper two-value level are to be removed by the "primary selection" which precedes the "secondary selection" as described previously, and only a real candidate defect is analyzed in detail by the controlling processor 19 and a real defect is stored along with the corresponding coordinates in the memory of the controlling processor 19.

Figure 10A:
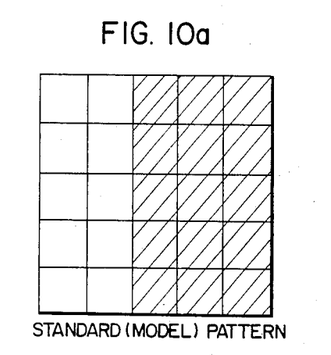
FIGS. 10a and 10b are diagrams used to explain typical pseudo defects due to the positioning error.
Figure 10B:
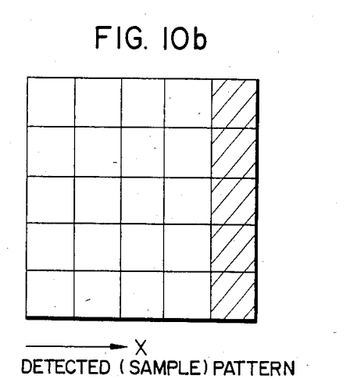

Next, the method of saving the positioning error in the "primary selection", that constitutes the principal portion of the present invention, will be described. FIGS. 10a and 10b are illustrations explaining a typical pseudo defect caused by the positional displacement, and a candidate defect is detected by an anti-coincidence detector similar to that shown in FIGS. 8a and 8b and FIG. 9. The candidate defect detector determines the defectiveness using information of only a small 3-by-3 area as mentioned previously and, therefore, a 2-bit displacement as in the case of FIGS. 10a and 10b causes an interrupt request to the controlling processor 19. The controlling processor 19 first reads out the contents of the analyzing memories 26 and 27. The analyzing memory 26 is a multi-value memory for storing a sample pattern, and it can be formed in various two-value arrangements by software. Each of the analyzing memories 26 and 27 stores an area larger than 3-by-3, and the state of the pattern around the candidate defect can be examined for analysis.

FIGS. 10a and 10b show an example of examining 5-by-5 picture elements around the candidate defect. The standard pattern (hatched portion) shown in FIG. 10a is moved in the X and Y directions and the amount of anticoincidence is evaluated. In this case, the assumption is made that a portion pushed out of the 5-by-5 area as a result of the movement is ignored, and for a portion which newly enters the 5-by-5 area, peripheral pattern information is preserved. Table 1 lists the relationship between the number of anti-coincident picture elements and the amount of movement when the sample pattern of FIG. 10b is moved relative to the model pattern of FIG. 10a in the X direction.

TABLE 1

| Movement of sample pattern in X direction | Number of anti-coincident picture elements |
| --- | --- |
| +4 | 15 |
| +3 | 15 |
| +2 | 15 |
| +1 | 15 |
| 0 | 10 |
| −1 | 5 |
| −2 | 0 |
| −3 | 5 |
| −4 | 10 |

In the table, the rightward movement of the sample pattern relative to the model patern in FIGS. 10a and 10b is defined to be positive. It can be seen from Table 1 that the sample pattern of FIG. 10b has a displacement of two picture elements in the X direction relative to the model pattern of FIG. 10a. Accordingly, it is concluded that the candidate defect detected by the candidate defect detector has actually been detected due to the occurrence of a 2-bit positional displacement and, thus, it is a pseudo defect which should not be determined as a defect. On this account, this anti-coincidence is not stored as a real candidate defect in the memory, but instead, correction for the +2 bit positional displacement is indicated to one of the buffer memories 22 with the position corrector (e.g., buffer memory 22-1), and the multiplexer 24 is switched to select the next buffer memory (e.g., buffer memory 22-2).

These are the operations for the positional displacement in the X direction. The similar correcting method can be used for a positional displacement in the Y direction or X and Y directions.

As a result of the foregoing analysis, if a candidate defect is found to be created due to the positioning error, the controlling processor 19 operates on the displacement corrector positions provided in the buffer memories 22 and 23 to correct the detected amount of displacement.

Figure 11:
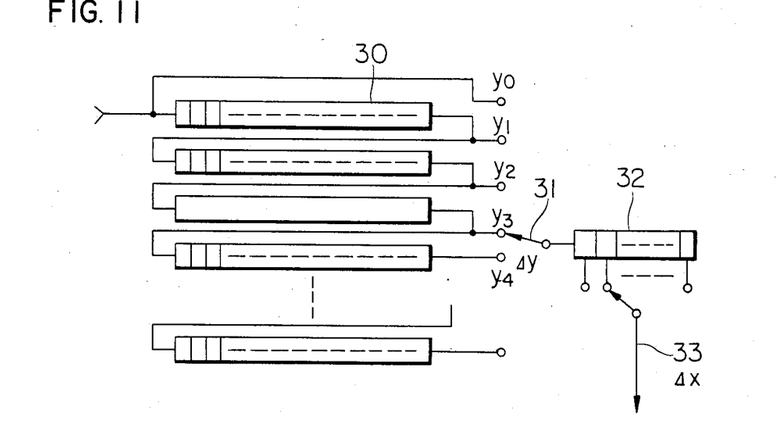
FIG. 11 is a block diagram showing an example of a positioning error corrector in an image buffer memory in a candidate defect detector.

FIG. 11 shows in block diagram of an example of the displacement corrector. A two-dimensional image detected by the image pickup unit 14A is assumed to be made up of 128-by-128 picture elements. The circuit arrangement includes a required number of 128-bit shift registers 30, equal in length to the number of picture elements in the lateral direction, connected in series, and one of the outputs of the shift registers is selected by a multiplexer 31 so that the image in the longitudinal direction can be delayed selectively. Alternatively, the displacement corrector may be included in the position correcting circuits 20 and 21, so that for the arrangement of the corrector included in the standard correction circuit, when the multiplexer 31 selects output $y_3$, the standard image data is delayed by three picture elements in the Y direction relative to the detected image data. Conversely, if the position correcting circuit 20 is arranged as shown in FIG. 11, the detected image data is delayed by three picture elements relative to the standard image data.

Switching of the multiplexer 31 allows the positioning between the detected image data and the standard image data in the longitudinal direction, i.e., in the Y direction. While in FIG. 11 the shift register 30 of 1 bit $\times$ 128 is shown, it is needless to say that a shift register of bit count of multi-level image signal by 128 may be employed for the position correction circuit 20 and the like. Similarly, the positional displacement in the X direction can be corrected by selecting one by the outputs of the serial-in/parallel-out shift register 32 by the multiplexer 33. Selection of the multiplexer 31 or 33 takes place in accordance with the amount of correction of displacement calculated by the controlling processor 19.

The analysis performed by the controlling processor 19 takes a very long time as compared with the scanning of image data if it is designed like a usual computer. The buffer memories 22 and 23 are used to retain image data during the analysis, and they are made up of shift registers with a capacity sufficient to store image data corresponding to at least the time needed for the analysis.

If a candidate defect is determined, as a result of analysis, to be a pseudo defect caused by the positional displacement, repositioning is carried out by the position correction circuit 20 or 21 in response to the command from the controlling processor 19 and, thereafter, the multiplexers 24 and 25 are switched so that the input to the defect detection circuit 28 is conducted through the buffer memory 22 (including the positional displacement corrector), and the detected image data stored during the analysis following the completion of positioning and the standard image data also stored during the analysis are received as input data. During the analyzing period, the defect detection circuit 28 is deactivated by the controlling processor 19, and it restarts its operation after the multiplexers 24 and 25 have been switched.

By use of the foregoing buffer memories, the loss of data is prevented while the detailed analysis goes on, and a defect determination circuit without missing of inspection can be realized. By using m-stage buffer memories, a maximum of m pseudo defects can be removed by the detailed analysis without the occurrence of an absent inspection area.

Due to condition (I) mentioned earlier, the positional displacement in one chip during the inspection of a photomask can be covered by image buffers as small as a few stages. Due to conditions (II) and (III), the image input to the defect detection circuit 28 can be restored to the initial state when a defect is detected or when the dicing area is scanned. On this account, the provision of the maximum number of stages needed for checking in one chip allows inspection for all chips. The cumulative positioning error caused by errors in the mechanical scanning system can be corrected by the position correction circuits 20 and 21.

While the invention has been described for a system employing an electronic positioning method, a more satisfactory result is obtained by moving the image pickup unit 14A in the X and Y directions in place of the foregoing method.

The analysis by the controlling processor 19 is carried out using contrasting image data as provided by the analyzing memory 26, and the amount of correction for the positional displacement can take a value smaller than one bit through the interpolating calculation for data between picture elements which have been sampled when image data produced by the image pickup unit 14A is converted by the A/D converter 14B into multi-level digital image data.

While the embodiment has been described on the assumption that the standard pattern data is derived from design data, it will be appreciated that the similar defect determination circuit can be used for an apparatus in which defects are detected on the basis of the comparison between two chips within one mask.

While in the foregoing embodiment the displacement correctors are provided for both the sample and model shift registers, another arrangement may be made such that a simple delay shift register is provided for one and the output port for the positive and negative positioning is determined solely from the other.

Through the foregoing analysis and operation for the "primary selection", pseudo defects caused by the positional displacement are separated from real candidate defects, and the number of candidate defects can be reduced significantly. In consequence, the real candidate defects can be analyzed more precisely by the controlling processor 19.

Figure 12:
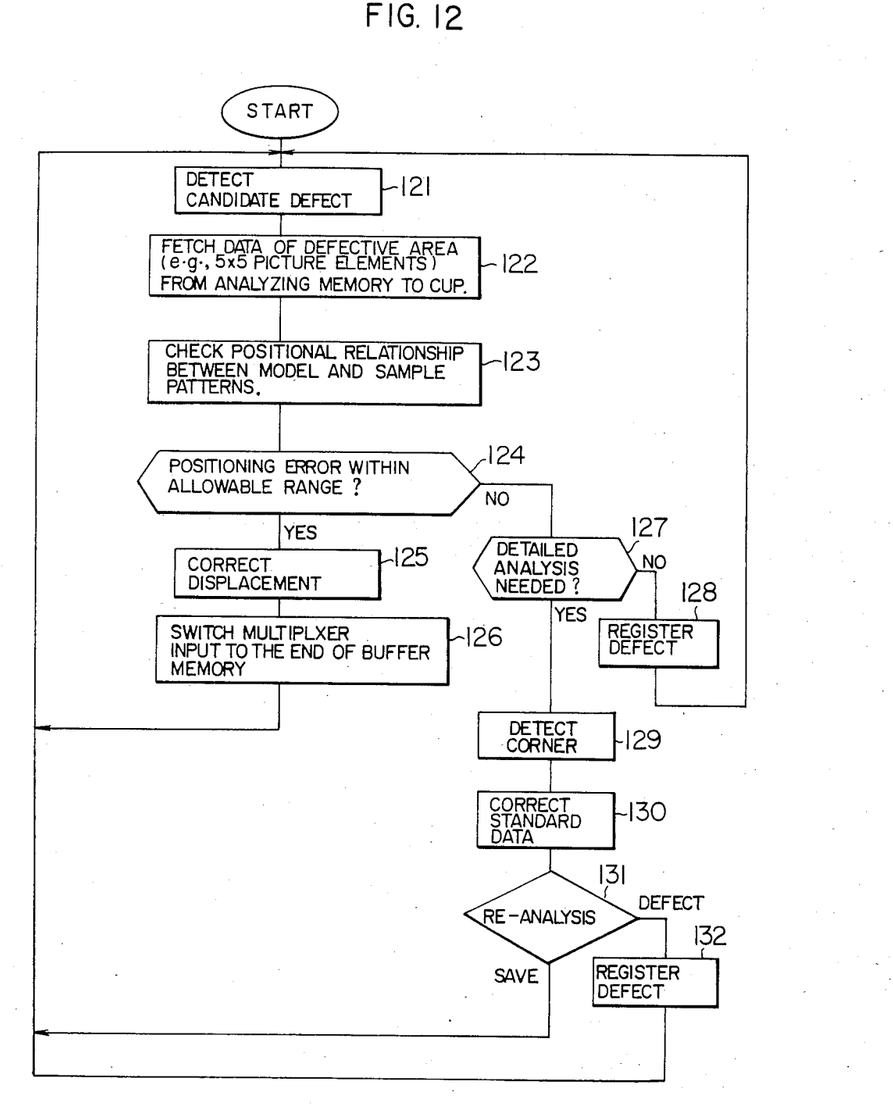
FIG. 12 is a flowchart showing the defect analysis carried out by a processor.
Figure 13A:
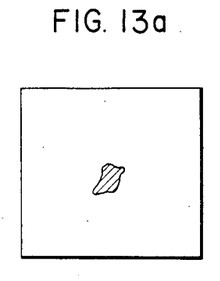
FIGS. 13a and 14a are illustrations showing examples of detected image data.
Figure 13B:
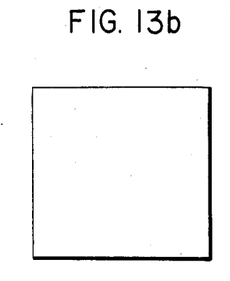
FIGS. 13b, 14b and 14c are illustrations showing examples of standard image data.
Figure 14A:
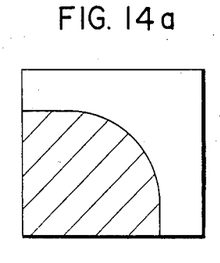
Figure 14B:
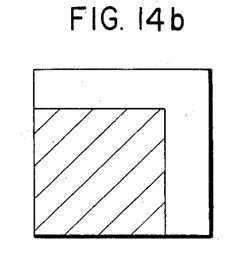
Figure 14C:
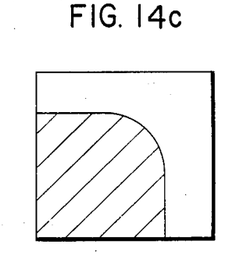

The feature of the present invention is to extract real candidate defects from numerous candidate defects through the "primary selection". The following describes the "primary selection" and the following detailed analysis ("secondary selection") using the flow-chart of FIG. 12. Steps 121 through 126 are processes, shown as an example, for saving a pseudo defect caused by the positional displacement, instead of registering it as a defect. In case the controlling processor 19 has determined in step 124 that the candidate is not a pseudo defect caused by the positional displacement, the operation proceeds to step 127. This can be the case of a defect, for example, as shown in FIG. 13a and FIG. 14a. FIG. 13a shows an isolated defect, and if such an isolated defect is detected against a blank model as shown in FIG. 13b, the operation proceeds from step 127 to step 128 so as to register the defect. In step 124, if anti-coincidence as shown in FIGS. 14a and 14b (angular pseudo defect of the pattern) is detected, the operation proceeds to step 127. FIG. 14a shows an example of detected image data, and such an angular pseudo defect occurs frequently due to physical etching or insufficient optical resolution. The standard image data is shown in FIG. 14b. In many cases, these types of pseudo defects at the corner are determined to be harmless and are saved. In this case, at step 127, the determination "more detailed analysis is required" is made, and the operation proceeds to step 129. In step 129, for example, the pattern is determined to be an angle based on the standard pattern of FIG. 14b through the use of a known pattern recognition technique, and in step 130 the standard image data is modified as shown in FIG. 14c. Namely, FIG. 14c is a modified version of FIG. 14b in accordance with the saving condition. Thereafter, in step 131, data of FIGS. 14a and 14c is analyzed again, and the candidate is determined to be a defect or it is saved as a pseudo defect basing on the two-dimensional information of both patterns or three-dimensional information including the two-dimensional information and illuminance of each picture element.

Two examples of defects have been shown. The detailed analysis can be carried out precisely because pseudo defects caused by the positional displacement are removed in step 124.

According to the present invention, as described above, defect determination is made while carrying out the positioning during the checking, whereby the structure of the defect finding device can be made simple and a significant cost reduction can be expected. After a defect has been detected, it is analyzed in detail to determine whether it is a real defect or a defect which is harmless practically. This allows the use of a sensitive candidate defect detector which has not been put into practice in the past due to anxiety of increasing erroneous determination. Consequently, the sensitivity of detection can be improved significantly, and a pattern checking apparatus which prevents erroneous determination can be provided. The present invention is significantly effective for the improvement of reliability, speed-up, and economy of pattern checking for, for example, patterns and the like used to fabricate semiconductor devices.

We claim:

1. A pattern checking apparatus comprising:
   scanning and imaging means for two-dimensionally scanning a pattern to be checked so as to provide sequential image signals;
   A/D converter means for converting the image signals sequentially received from said scanning and imaging means into digital image signals;
   standard data generating means for sequentially generating standard pattern data corresponding to said pattern to be checked;
   first buffer memory means for temporarily storing the digital image signal received from said A/D converter means;
   second buffer memory means for temporarily storing the standard pattern data from said standard data generating means;
   candidate defect detecting means for comparing the digital image signals and the standard pattern data to detect a candidate defect on the basis of detection of anti-coincidence therebetween;
   a first analyzing memory for storing the digital image signal for a portion of said pattern to be checked inclusive of the candidate defect and signals relating to points around the candidate defect, the entry of the digital image signals into said first analyzing memory being stopped when said candidate defect detecting means detects the candidate defect;
   a second analyzing memory for storing the standard pattern data for the portion of said pattern to be checked inclusive of the portion corresponding to the candidate defect and signals relating to points therearound; and
   controlling processor means responsive to detection of the candidate defect by said candidate defect detecting means for reading and comparing the digital image signals stored in said first analyzing memory and the standard pattern data stored in said second analyzing memory to determine the amount of positioning error therebetween when a positioning error exists, for reading at least one of the digital image signals from said first buffer memory means and the standard pattern data from said second buffer memory means while relatively correcting said positioning error, and for entering the relatively corrected digital image signal or standard pattern data into said candidate defect detecting means and said first or second analyzing memory, so that in reading and comparing again the digital image signal stored in said first analyzing memory and the standard pattern data stored in said second analyzing memory, the inclusion of positioning errors as candidate defects is minimized and a candidate defect in a practically allowable error range is removed from the remaining candidate defects, thereby to detect a true defect.

2. A pattern checking apparatus according to claim 1, further comprising a multiplexer connected between said first buffer comprising a multiplexer connected between said first also said first analyzing memory for performing the correction of said positioning error amount.

3. A pattern checking apparatus according to claim 1, wherein each of said first and second buffer memory means is provided as a shift-register.

4. A pattern checking apparatus according to claim 1, wherein each of said first and second analyzing memories is provided in the form of a shift-register.

5. A pattern checking apparatus according to claim 1, wherein said candidate defect detecting means includes means for comparing the digital image signal with a plurality of threshold values to obtain a plurality of binary image data and for detecting anti-coincidence between the plural binary image data and said standard pattern data, the detected anti-coincidences being OR-ed by an OR circuit.

6. A pattern checking apparatus according to claim 1, wherein said candidate defect detecting means is non-sensitive to a very small positional displacement in detecting the anti-coincidence.

7. A pattern checking apparatus according to claim 1, further comprising a controllable position correction circuit provided as part of said first buffer memory means for shifting the position of said digital image signals under control of said controlling processor means.

8. A pattern checking apparatus according to claim 1, further comprising a multiplexer connected between said second buffer memory means and said candidate defect detecting means and also said second analyzing memory for performing the correction of said positioning error amount.

9. A pattern checking apparatus according to claim 1, further comprising a controllable position correction circuit provided as part of said second buffer memory means for shifting the position of said digital image signals under control of said controlling processor means.

* * * * *